United States Patent

Baudy et al.

Patent Number: 5,864,040
Date of Patent: Jan. 26, 1999

[54] BENZIMIDAZOLE PHOSPHONO-AMINO ACIDS

[75] Inventors: Reinhardt B. Baudy, Doylestown, Pa.; Michel Bekhazi, Pointe Claire, Canada; Brian J. Bushell, deceased, late of Fareham, United Kingdom; by Judith Marion Bushell, executrix, Fareham, United Kingdom; Gloria Cheal, Ville LaSalle, Canada

[73] Assignee: American Home Products Corporation, Madison, N.J.

[21] Appl. No.: 771,547

[22] Filed: Dec. 23, 1996

Related U.S. Application Data

[60] Provisional application No. 60/010,012 Jan. 11, 1996.
[51] Int. Cl.$^6$ .................................................. C07D 236/14
[52] U.S. Cl. .............................................. 548/113
[58] Field of Search .............................................. 548/113

[56] References Cited

U.S. PATENT DOCUMENTS 5,124,319  6/1992  Baudy et al. .............................. 514/80

*Primary Examiner*—Patricia L. Morris
*Attorney, Agent, or Firm*—Arnold S. Milowsky

[57] ABSTRACT

This invention provides a process for the preparation of a compound of formula I

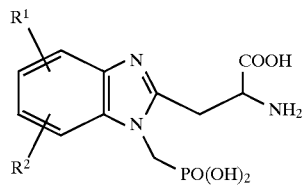

wherein $R^1$ and $R^2$ are each, independently, hydrogen, alkyl, alkoxy, trifluoromethyl, trifluoromethoxy, methanesulfonylamino, acetylamino, halo, cyano, nitro, or when taken together $R^1$ and $R^2$ represent a methylenedioxy or ethylenedioxy moiety;

or a pharmaceutically acceptable salt thereof.

4 Claims, No Drawings

BENZIMIDAZOLE PHOSPHONO-AMINO ACIDS

BACKGROUND OF THE INVENTION

This application claims the benefit of U.S. Provisional Application No. 60/010,012, filed Jan. 11, 1996.

L-Glutamate and L-aspartate, the endogenous acidic amino acids, have been firmly established as major excitatory neurotransmitters. The action of these excitatory amino acids is mediated by several distinct receptor subtypes of which the best studied one is the N-methyl-D-aspartate (NMDA) receptor. Excessive activation of the NMDA receptor complex may cause neuronal overstimulation with pathological consequences. Experimental evidence suggests that a prolonged, agonist-evoked conductance of the NMDA-gated ion channel permits an abnormal enhancement of calcium entry, and the resulting increased levels of intracellular calcium play a pivotal, deleterious role in the excitotoxic neuronal damage, neurodegeneration, and delayed neuronal death.

Excitatory amino acids have been implicated in neuropathologies of traumatic, endogenous genetic, and environmental origin. Brain damage associated with anoxia, hypoglycemia, traumatic injury, stroke, epilepsy, specific metabolic defects, and some chronic neurodegenerative diseases is, to a large extent, produced by excitotoxic mechanisms.

A number of studies have demonstrated that a blockade of the NMDA-subclass receptor significantly reduces a neuronal damage and loss which occurs in animal models mimicking a variety of neuropathological situations. These observations strongly indicate that NMDA antagonists offer effective neuroprotection in several clinical settings. Thus, agents antagonizing the excitotoxic effects mediated by the NMDA receptor are beneficial in the treatment of ischemic conditions, stroke, brain or spinal cord injury, and generally, in patients with escalating levels of excitatory transmitters. Specific applications also include therapy of senile dementia Alzheimer-type, parkinsonian dementia complex, Huntington's chorea, and other dominant or recessive spinocerebellar degenerations where NMDA antagonists prevent or retard the progression of the disease.

U.S. Pat. No. 5,124,319 discloses benzimidazole phosphono-amino acids that are NMDA antagonists useful in the treatment and prevention of central nervous system related pathological conditions resulting from overstimulation by excitatory amino acids.

DESCRIPTION OF THE INVENTION

This invention provides a process for preparing compounds of formula I

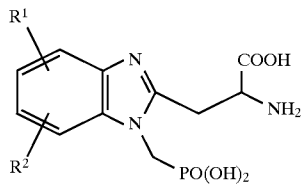

I wherein $R^1$ and $R^2$ are each, independently, hydrogen, alkyl of 1–6 carbon atoms, alkoxy of 1–6 carbon atoms, trifluoromethyl, trifluoromethoxy, methanesulfonylamino, acetylamino, halo, cyano, nitro, or when taken together $R^1$ and $R^2$ represent a methylenedioxy or ethylenedioxy moiety;

or a pharmaceutically acceptable salt thereof.

The compounds within the scope of the invention by virtue of their configuration, contain a chiral center. Such center can contain either the D or L configuration or can be racemic with respect to such center. Accordingly, the process described herein can be used to make compounds of formula I having the D-configuration, or the L-configuration at the chiral center, as well as racemic compounds of formula. It is preferred that the chiral center of the a-amino acid has the D configuration.

The terms alkyl of 1–6 carbon atoms and alkoxy of 1–6 carbon atoms include both straight chain as well as branched carbon chains. The term halo refers to fluoro, chloro, bromo and iodo.

The pharmaceutically acceptable salts are those derived from pharmaceutically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds of the invention as phosphono-carboxylic acids are capable of forming alkali metal and alkaline earth carboxylates and carboxylates of pharmaceutically acceptable cations derived from ammonia or a basic amine. Examples of the latter include but are not limited to cations such as ammonium, mono-, di-, and tiimethylammonium, mono-, di- and triethylammonium, mono-, di-and tripropylammonium (iso and normal), ethyldimethylammonium, benzyldimethylammonium, cyclohexylammonium, benzylammonium, dibenzylammonium, pipeiidinium, moipholinium, pyrrolidinium, piperazinium, 1-methylpiperidinium, 4-etohylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmonoethanolammonium, and the like.

The compounds prepared by the process described herein are useful in the treatment and prevention of central nervous system related pathological conditions resulting from overstimulation by excitatory amino acids, as described in U.S. Pat. No. 5,214,319, which is incorporated by reference.

The compounds of formula I can be prepared as illustrated below in Scheme 1.

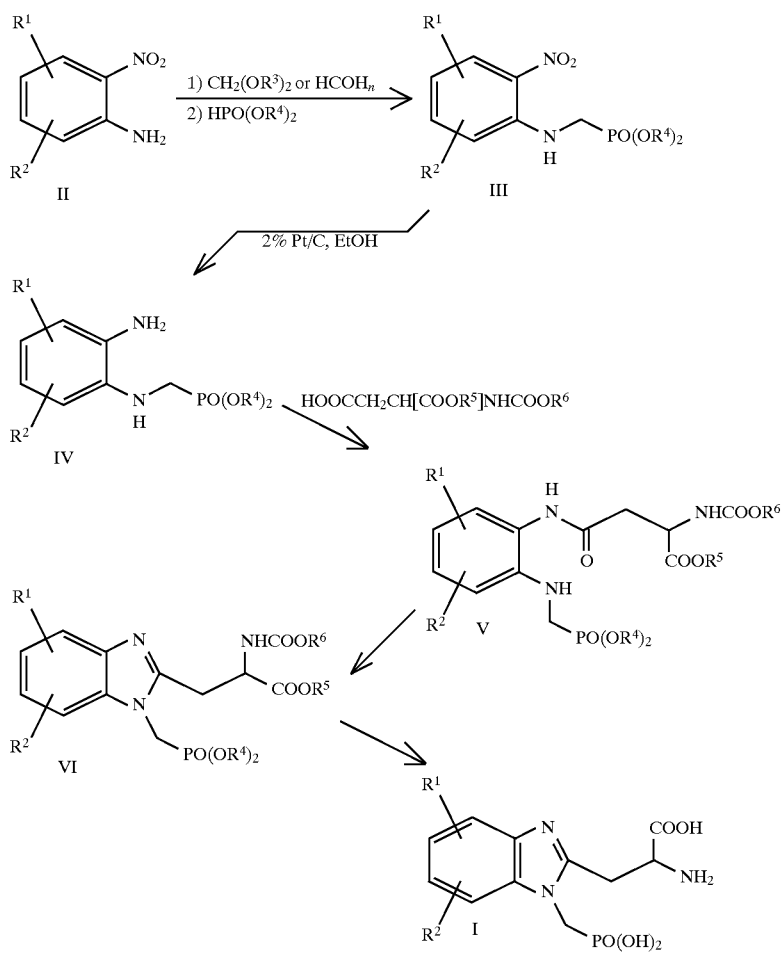

Scheme 1

With reference to reaction scheme 1, an appropriately substituted 2-nitroaniline II is reacted with an alokozoxymethane, in which $R_3$ is preferably alkyl of 1–6 carbon atoms, or paraformaldehyde, followed by the addition of dialkyl- or dibenzyiphosphite. The resulting phosphonate ester III is hydrogenated in the presence of a suitable catalyst such as rhodium, palladium or platinum to yield the aniline derivative IV. A coupling step, catalyzed by a coupling agent such as 1,1'-carbonyldiimidazole (CDI), isobutylchloroformate, 1,3-dicyclohexylcarbodiimide (DCC), 1-hydroxybenzotriazole/ 1,3-dicyclohexylcarbodiimide (HOBT/DCC), 2-(1-hydroxybenziotiiazole-1-yl)-1,1,3,3-tetramethyluronium hexafluorophosphate (HBTU), 2-(1H-benzotriazole-1-yl)-N,N,N'N'-tetramethyluronium tetrafluorobotate (TBTU) or bis(2-oxo-3-oxazolidinyl)phosphinic chloride (BOP.Cl), between IV and an appropriately protected d-aspartic acid, in which $R_5$ and $R^6$ can be independently selected from alkyl of 1–6 carbon atoms, phenyl, benzyl, carbaotnoyl, leads to V. An intramolecular cyclization of V using an acid catalyst such as trifluoroacetic acid, hydrochloric acid or p-toluenesulfonic acid generates readily the benzimidazole VI. Deprotection, using and agent such as HCI, HBr, or tiimethylsilyl halide, of VI yields the desired compound I as an acid addition salt, which upon dissolution in water followed by the addition of acetone leads to the free phosphono α-amino acid I. As seen from Scheme 1, the compound of formula V is an intermediate useful in the preparation of the compound of formula I.

The following illustrates a preferred method for the preparation of a of representative compound of formula I.

Example 1

(−)-(R)-alpha-Amino-5-chloro-1-(phosphonomethyl)-1H-benzimidazole-2-propanoic acid Step (1) Preparation of [(4-Chloro-2-nitro-phenylamino)-methyl]-phosphonic acid diethyl ester.

(III: $R_1$=H, $R_2$=4-Chloro)

With stirring and under a nitrogen atmosphere 4-chloro-2-nitroaniline (5 g, 28.9 mmole) was dissolved in diethylphosphite (21.44 g, 155 mmole), followed by the addition of a solution of sulfuric acid (0.1 mL) and water (0.1 mL). Under a continuous flow of nitrogen the solution was heated to 95° C., after which diethoxymethane (9.05 g, 86.8 mmole) was added in a dropwise manner over a period of 1.5 hours while maintaining the temperature between 93°–97° C. Once all the diethoxymethane was added, the reaction was kept at 95°–105° C. for another hour after which the mixture was cooled to 45°–50° C. and cold water (70 mL) was added over 20 minutes. The resulting suspension was filtered, washed first with water (10 mL), then with heptane (10 mL). The obtained orange solid was dried at 30°–40° C. for 16 hours to yield 8.85 g (95%) of the title compound, mp 94°–5° C.

Elemental Analysis for: $C_{11}H_{16}ClN_2O_5P$.
Calcd: C, 40.94; H, 5.00; N, 8.68.
Found: C, 40.69; H, 4.74; N, 8.55.

Step (2) Preparation of [(2-Amino-4-chloro-phenylamino)-methyl]-phosphonic acid diethyl ester.

(IV: $R_1$=H, $R_2$=4-Chloro, $R_4$=Ethyl)

A solution of [(4-Chloro-2-nitro-phenylamino)-methyl]-phosphonic acid diethyl ester (45g, 0.139 moles) in ethanol (500 mL) was treated under nitrogen at once with 5% Platinum on carbon (1.125 g) and then hydrogenated at 30° C. until the hydrogen uptake ceased. After purging the reaction vessel with nitrogen the reaction mixture was filtered through solka floc. The filter cake was washed with ethanol (100 mL) and the filtrate was used as such for next step without purification.

Step (3) Preparation of (R)-2-Benzyloxycarbonylamino-N-{5-chloro-2-[(diethoxy-phosphorylmethyl)-amino]-phenyl}-succinamic acid benzyl ester.

(V: $R_1$=H, $R_2$=5-Chloro, $R_4$=Ethyl)

The above ethanolic solution was evaporated to a volume of 100 mL under reduced pressure at a bath temperature of 60° C., after which toluene (200 mL) was added and the evaporation continued to a volume of 100 mL. This solution was added over a period of 1 hour to a solution of N-α-CBz-D-aspartic acid-α-benzyl ester (49.862 g, 0.139 moles) and DCC (34.515 g, 0.167 moles) in toluene (500 mL) at ambient temperature. After stirring the reaction mixture for one hour at room temperature it was cooled to 5°–10° C., filtered and washed with toluene (2×40 mL). The filtrate was used in the next step without purification.

Step (4) Preparation of (R)-2-Benzyloxycarbonylamino-3-[5-chloro-1-(diethoxy-phosphorylmethyl)-1H-benzoimidazol-2-yl]-propionic acid benzyl ester.

(VI: $R_1$=H, $R_2$=5-Chloro, $R_4$=Ethyl)

Trifluoroacetic acid (15.9 g, 0.139 moles) was added to the above filtrate and the reaction mixture heated to reflux for 4 hours, after which the mixture was cooled to 60° C. and diluted with hot water (100 mL). The organic layer was separated, washed two more times with water (100 mL) and evaporated under vacuo. The resulting residue was used for the next step without purification.

Step (5) Preparation of (−)-(R)-alpha-Amino-5-chloro-1-(phosphono methyl)-1H-benzimidazole-2-propanoic acid.

(I: $R_1$=H, $R_2$=5-Chloro)

The above residue was diluted with concentrated hydrochloric acid (750 mL) and water (100 mL). The resulting mixture was heated to reflux for four hours, after which it was cooled to ambient temperature and washed with toluene (100 mL). The separated aqueous layer was treated at once with Nuchar (6 g) and stirred at 50°–60° C. for 30 minutes, after which it was filtered through celite. The filtrate was evaporated in vacuo. The residue was dissolved in water (150 mL) at 50° C. The pH of the solution was adjusted with the addition of ammonia to pH 3 and the resulting suspension diluted with acetone (3–4 L) and left at ambient temperature for one hour. The suspension was filtered and the cake washed with water (250 mL) and acetone (250 mL). The product was dried in a vacuum oven at 60° C. for 16 hours to yield 20.7 g (45%) of the title compound, mp 212°–20° C. (Decomposition).

Elemental Analysis for: $C_{11}H_{13}ClN_3O_5P \cdot 0.8\ H_2O$.
Calcd: C, 37.95; H, 4.22; N, 12.07.
Found: C, 37.99 H, 4.03; N, 12.00.

What is claimed is:

1. A process for the preparation of a compound of formula I

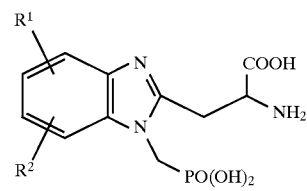

wherein $R^1$ and $R^2$ are each, independently, hydrogen, alkyl of 1–6 carbon atoms, alkoxy of 1–6 carbon atoms, trifluoromethyl, trifluoromethoxy, methanesulfonylamino, acetylamino, halo, cyano, nitro, or when taken together $R^1$ and $R^2$ represent a methylenedioxy or ethylenedioxy moiety;

or a pharmaceutically acceptable salt thereof, which comprises a) heating a nitroaniline of formula with II

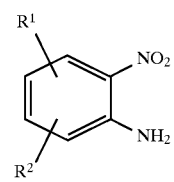

with $HPO(OR_4)_2$ and either $CH_2(OR^3)_2$ or paraformaldehyde to provide a compound of formula III

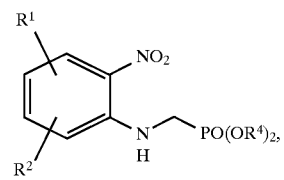

wherein $R^3$ is alkyl of 1–6 carbon atoms, and $R^4$ is alkyl of 1–6 carbon atoms or benzyl;

b) hydrogenating the compound of formula III with a rhodium, platinum, or palladium based catalyst suitable to reduce nitrophenyl group to an aniline group to provide a compound of formula IV,

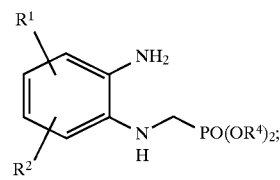

c) warming a solution of the compound of formula IV and a suitable solvent with a protected aspartic acid derivative of the formula, $D-HO_2CCH_2CH[CO_2R^5]NHCO_2R^6$, in the presence of a coupling agent selected from the group consisting of 1,1'-carbonyldiimidazole, isobutylchloroformate, 1,3-dicyclohexylcarbodiimide, 1-hydroxybenzotriazole/1,3-dicyclohexylcarbodiimide, 2-(1-hydroxybenziotriazole-1-yl)-1,1,3,3-tetramethyluronium hexafluorophosphate, 2-(1H-benzotriazole-1-yl)-N,N,N'N'-tetramethyluronium tetrafluorobotate, and bis(2-oxo-3-oxazolidinyl)

phosphinic chloride to provide a compound of formula V, $$\text{V}$$

R¹—(benzene ring)—N(H)—C(=O)—CH₂—CH(NHCOOR⁶)(COOR⁵); with R²—(benzene)—NH—CH₂—PO(OR⁴)₂ wherein $R^5$ and $R^6$ are each, independently, alkyl of 1–6 carbon atoms, phenyl, benzyl, or carbamoyl;

d) heating the compound of formula V in the presence of an acid catalyst to provide a compound of formula VI, $$\text{VI}$$

benzimidazole with R¹, R² on ring; N-substituent CH₂—PO(OR⁴)₂; 2-substituent CH₂—CH(NHCOOR⁶)(COOR⁵);

and e) heating the compound of formula VI in the presence of an acid, and subsequent neutralization of the resulting solution.

2. The process of claim 1 wherein the acid catalyst used in step d is trifluoroacetic acid, hydrochloric acid or p-toluenesulfonic acid.

3. A process for the preparation of a compound of formula I $$\text{I}$$

benzimidazole with R¹, R²; N-substituent CH₂—PO(OH)₂; 2-substituent CH₂—CH(NH₂)(COOH);

wherein $R^1$ and $R^2$ are each, independently, hydrogen, alkyl of 1–6 carbon atoms, alkoxy of 1–6 carbon atoms, trifluoromethyl, trifluoromethoxy, methanesulfonylamino, acetylamino, halo, cyano, nitro, or when taken together $R^1$ and $R^2$ represent a methylenedioxy or ethylenedioxy moiety;

or a pharmaceutically acceptable salt thereof, which comprises a) heating the compound of formula V $$\text{V}$$

(same structure as above)

wherein $R^4$ is alkyl of 1–6 carbon atoms or benzyl; and $R^5$ and $R^6$ are each, independently, alkyl of 1–6 carbon atoms, phenyl, benzyl, or carbamoyl;

in the presence of an acid catalyst to provide a compound of formula VI, $$\text{VI}$$

(structure as above)

b) heating the compound of formula VI in the presence of an acid, and subsequent neutralization of the resulting solution.

4. A process for the preparation of a compound of formula VI $$\text{VI}$$

(structure as above)

wherein $R^1$ and $R^2$ are each, independently, hydrogen, alkyl of 1–6 carbon atoms, alkoxy of 1–6 carbon atoms, trifluoromethyl, trifluoromethoxy, methanesulfonylamino, acetylamino, halo, cyano, nitro, or when taken together $R^1$ and $R^2$ represent a methylenedioxy or ethylenedioxy moiety; $R^4$ is alkyl of 1–6 carbon atoms or benzyl; and $R^5$ and $R^6$ are each, independently, alkyl of 1–6 carbon atoms, phenyl, benzyl, or carbamoyl;

which comprises, a) warming a solution of the compound of formula IV $$\text{IV}$$

R¹, R²-substituted benzene with NH₂ and NH—CH₂—PO(OR⁴)₂;

and a suitable solvent with a protected aspartic acid derivative of the formula, D-HO₂CCH₂CH[CO₂R⁵]NHCO₂R⁶, in the presence of a coupling agent selected from the group consisting of 1,1'-carbonyldiimidazole, isobutylchloroformate, 1,3-dicyclohexylcarbodiimide, 1-hydroxybenzotriazole/1,3-dicyclohexylcarbodiimide, 2-(1-hydroxybenziotriazole-1-yl)-1,1,3,3-tetramethyluronium hexafluorophosphate, 2-(1H-benzotriazole-1-yl)-N,N,N'N'-tetramethyluronium tetrafluorobotate, and bis(2-oxo-3-oxazolidinyl)phosphinic chloride to provide a compound of formula V, $$\text{V}$$

(structure as above)

and b) heating the compound of formula V in the presence of an acid catalyst to provide a compound of formula VI.

* * * * *